US008268351B2

(12) United States Patent
Thumbeck et al.

(10) Patent No.: US 8,268,351 B2
(45) Date of Patent: Sep. 18, 2012

(54) MATRIX FILM TABLET WITH CONTROLLED RELEASE OF A NATURAL MIXTURE OF CONJUGATED ESTROGENS

(75) Inventors: Bernd Thumbeck, Nordstemmen (DE); Klaus Budde, Neustadt (DE); Gerhard Kristen, Burgdorf (DE); Margit Wiards, Barsinghausen (DE)

(73) Assignee: Abbott Products GmbH, Hanover (DE)

( * ) Notice: Subject to any disclaimer, the term of this patent is extended or adjusted under 35 U.S.C. 154(b) by 479 days.

(21) Appl. No.: 10/866,094

(22) Filed: Jun. 14, 2004

(65) Prior Publication Data

US 2005/0019408 A1    Jan. 27, 2005

Related U.S. Application Data

(63) Continuation of application No. PCT/EP02/14103, filed on Dec. 12, 2002.

(30) Foreign Application Priority Data

Dec. 14, 2001   (EP) ..................................... 01129830

(51) Int. Cl.
*A61K 9/26* (2006.01)
(52) U.S. Cl. ........ 424/469; 424/464; 424/468; 424/470; 424/472; 424/474; 424/475; 424/479; 424/480; 424/484; 424/488; 514/182
(58) Field of Classification Search .................. 424/472, 424/400, 484, 485, 489, 464, 465
See application file for complete search history.

(56) References Cited

U.S. PATENT DOCUMENTS

| | | | | |
|---|---|---|---|---|
| 3,753,767 A | * | 8/1973 | Becker ........................... | 427/2.2 |
| 4,753,803 A | | 6/1988 | Klug et al. | |
| 5,108,995 A | * | 4/1992 | Casper .......................... | 514/170 |
| 5,208,225 A | * | 5/1993 | Boissonneault et al. ....... | 514/178 |
| 5,458,887 A | * | 10/1995 | Chen et al. ..................... | 424/464 |
| 5,814,624 A | * | 9/1998 | Ban et al. ....................... | 514/170 |
| 5,908,638 A | * | 6/1999 | Huber et al. ................... | 424/465 |
| 6,022,554 A | * | 2/2000 | Lee et al. ....................... | 424/423 |
| 6,120,803 A | * | 9/2000 | Wong et al. .................... | 424/473 |
| 6,569,844 B1 | * | 5/2003 | Schwarz et al. ............... | 514/176 |
| 6,632,451 B2 | * | 10/2003 | Penhasi et al. ................. | 424/464 |
| 6,706,283 B1 | | 3/2004 | Appel et al. | |
| 6,878,387 B1 | | 4/2005 | Petereit et al. | |
| 6,884,793 B2 | * | 4/2005 | Dittgen et al. ................. | 514/170 |
| 2001/0034340 A1 | * | 10/2001 | Pickar ........................... | 514/177 |

FOREIGN PATENT DOCUMENTS

| | | |
|---|---|---|
| CA | 2263757 A1 | 3/1998 |
| CA | 2263904 A1 | 3/1998 |
| EP | 0322020 A | 6/1989 |
| JP | 62-087518 A | 4/1987 |
| JP | 2000229846 A | 8/2000 |
| JP | 2000-516938 A | 12/2000 |
| WO | 97 04752 A | 2/1997 |
| WO | WO9704752 * | 2/1997 |
| WO | 98/08525 A1 | 3/1998 |
| WO | 98/08526 A1 | 3/1998 |
| WO | 00/19984 A2 | 4/2000 |

OTHER PUBLICATIONS

Hydroxypropylmethylcellulose, Fiedler Encyclopedia of Excipients, 5th ed., pp. 855-856 (2000).
Medscape, Monograph—Estrogen, Conjugated USP, (Jan. 2009).
Microcrystalline Cellulose, Fiedler Encyclopedia of Excipients, 5th ed., pp. 380-381 (2000).
Premarin (conjugated estrogen) tablet firm coat, Wyeth Pharmaceuticals, Inc., available at http://dailymed.nlm.nih.gov/dailymed/drugInfo.cfm?id=17328. (May 2008).
Kamel et al, Pharmaceutical significance of cellulose: a review, eXPRESS Polymer Letters, vol. 2, 2008, No. 11, pp. 758-778.
Siepmann et al., Modeling of drug release from delivery systems based on hydroxypropyl methylcellulose (HPMC), Advanced Drug Delivery Reviews, vol. 48, 2001, pp. 139-157.
Parmentier, Auxiliary Agents for direct tabletting—a survey, Pharma International, 1998, pp. 18-23.
Degussa, Pharmacopoeial monographs and Drug Master Files, PharmaPolymers Jun. 2004, pp. 1-4.
Degussa, Scientific names according to IUPAC regulations, Jun. 2004, p. 1.
European Pharmacopoeia 5.0, pp. 983-984, chapter "Amino Methacrylate A", Jan. 2005.
European Pharmacopoeia; Jan. 2005; Monograph 1512: Estrogens, conjugated, pp. 1539-1541.
United States Pharmacopoeia, Conjugated estogens, pp. 1-5, Jan. 2005.
Degussa, "Creating Essentials," Sep. 2004, pp. 1-4.
Ritschel, W.A., et al., Die Tablette: Handbuch der Entwicklung, Herstellung und Qualitatssicherung [textbook of pharmaceutical technology]; Aulendorf, Ed. Cantor Verl., 2., 2002; pp. 71-72, 95-97 and 108, chapter "Cellulose" (English translation).
Rompp [chemical dictionary]; online version, last update Aug. 2005, chapter "Cellulose derivatives", p. 1. (English translation).
Pharmazeutische Pellets—Herstellung, Eigenschaften und Anwendung [textbook of pharmaceutical technology]; Peter Kleinbudde, 2003, chapter "Microcrystalline Cellulose", pp. 1-2. (English translation).
Nyqvist, H., et al., Studies on the physical properties of tablets and tablet excipients: I. Adsorption of drugs to cellulose used in tablets, Acta Pharm Suec, vol. 15, 1978, No. 2, pp. 150-159.

* cited by examiner

*Primary Examiner* — Robert A Wax
*Assistant Examiner* — Hasan Ahmed
(74) *Attorney, Agent, or Firm* — Lisa V. Mueller; Michael Best & Friedrich LLP

(57) ABSTRACT

A pharmaceutical matrix film tablet with controlled release of natural mixtures of conjugated estrogens which have been obtained from the urine of pregnant mares.

25 Claims, No Drawings

MATRIX FILM TABLET WITH CONTROLLED RELEASE OF A NATURAL MIXTURE OF CONJUGATED ESTROGENS

CROSS REFERENCE TO RELATED APPLICATIONS

This application is a continuation of international patent application no. PCT/EP02/14103, filed Dec. 12, 2002, designating the United States of America and published in German as WO 03/051336, the entire disclosure of which is incorporated herein by reference. Priority is claimed based on European Patent Application No. EP 01129830.4, filed Dec. 14, 2001.

BACKGROUND OF THE INVENTION

The present invention relates to a pharmaceutical matrix film tablet with controlled release of natural mixtures of conjugated estrogens which have been obtained from the urine of pregnant mares.

Estrogens are used in medicine for hormone replacement therapy. In particular, estrogen mixtures are used for the treatment and prophylaxis of the disorders of the climacteric period which occur in women after natural or artificial menopause. In this case, natural mixtures of conjugated estrogens such as are found in the urine of pregnant mares have proved particularly effective and readily compatible.

The dissolved solids content in the urine of pregnant mares (=pregnant mares' urine, abbreviated hereafter as "PMU") can naturally vary within wide ranges, and may generally lie in a range of 40 to 90 g dry matter per liter. In addition to urea and other usual urine contents, phenolic constituents, e.g. cresols and dihydro-3,4-bis[(3-hydroxyphenyl)methyl]-2 (3H)-furanone, known as HPMF, are contained in the solids content of the PMU. The natural mixture of estrogens contained in the PMU is largely present in conjugated form, e.g. as sulfuric acid semi-ester sodium salt (abbreviated hereafter as "sulfate salt"). The content of conjugated estrogens (abbreviated hereafter as "CE"), calculated as estrogen sulfate salt and relative to dry matter, may be between 0.3 and 1% by weight.

Upon separation of the undesirable accompanying substances, such as urea and in particular cresols and HPMF, usually extracts are obtained from the PMU which contain the conjugated estrogens from pregnant mares' urine (PMU) in dissolved form. More recent methods obtain natural mixtures of these conjugated estrogens (CE) by solid-phase extraction of the mixture of conjugated estrogens from pregnant mares' urine e.g. on RP silica gel (U.S. Pat. No. 5,814,624) or on non-ionic semipolar polymeric adsorption resins (U.S. Pat. No. 5,723,454). Although the undesirable accompanying substances can be separated out of the PMU more effectively and more efficiently with these methods and aqueous extracts of the CE of good quality can be obtained, the concentration of the CE in the extract is subject to certain unavoidable fluctuations, since PMU, as a natural starting material for obtaining the CE per se is subject to natural fluctuations in quality due to its origin, storage, transport and any pre-processing.

Due to the properties of the extracts of natural mixtures of conjugated estrogens obtained in this way and in particular also due to the accompanying substances which usually still remain therein after working-up, it is not easy to convert these extracts galenically into solid pharmaceutical preparations of reliable quality. In the production of solid pharmaceutical preparations of natural mixtures of conjugated estrogens from CE-containing extracts, however a constant quality and dose strength of the preparation and a predetermined release profile must be ensured. The natural fluctuations in the content of conjugated estrogens in the extracts used for the production of pharmaceutical preparations which occur dependent on the yield and quality of the PMU starting material therefore have to be compensated for by suitable galenic processing, so that solid pharmaceutical preparations of natural mixtures of conjugated estrogens with constant quality, dose strength and also predetermined release profile can be provided.

SUMMARY OF THE INVENTION

It is thus an object of the present invention to provide improved solid pharmaceutical preparations of natural mixtures of conjugated estrogens which meet the set pharmaceutical requirements and can be produced in simple manner in a constant quality, dose strength and also with a predetermined release profile.

In particular, it is an object of the invention to provide solid pharmaceutical preparations of natural mixtures of conjugated estrogens which have been obtained from pregnant mares' urine which contain the natural mixture of conjugated estrogens as active component in defined form and concentration and in a homogeneous distribution in a matrix film tablet produced by tabletting, for example direct tabletting, of powdery or particulate raw materials which contain active substance and have a predetermined release profile.

It has now surprisingly been found that powdery or granular dry extracts or preformulations of natural mixtures of conjugated estrogens (CE) obtained from PMU, which have been produced by spraying an aqueous CE-containing solution extract on to a solid pharmaceutical support material fluidized in a fluidized bed in a homogeneous distribution and defined concentration are dry extracts or preformulations of high quality, which can be processed further galenically by tabletting, for example direct tabletting, if desired also after prior granulation, easily to form matrix tablets with a defined and homogeneous active-substance distribution.

The present invention therefore relates to a pharmaceutical matrix film tablet with controlled active-substance release, the tablet being distinguished by the following features:
(a) a water-swellable matrix core,
   (i) which contains embedded as active substance a natural mixture of conjugated equine estrogens in the form of a pharmaceutically preformulated homogeneous dry extract,
      the dry extract having a standardized active-substance content (relative to the main hormone constituents) of the mixture of natural conjugated equine estrogens defined per amount of support material, and the active-substance content is applied by spraying from an aqueous solution on to a powdery and/or granular pharmaceutical support material from the group of microcrystalline celluloses or a mixture of microcrystalline cellulose with lactose, and drying;
   (ii) the water-swellable matrix of which is formed from a composition which can be made into tablets, which comprises at least one matrix former from the group of gel-forming pharmaceutical polymers, in particular a gel-forming pharmaceutical polymer from the group of cellulose and/or starch derivatives, and also optionally one or more further pharmaceutical tabletting auxiliaries from the group of other matrix formers, such as in particular microcrystalline celluloses, fillers, binding agents, water-soluble osmotic agents and lubricants, such as in particular sliding agents, glidants and/or mould lubricants
and that the tablet
(b) is provided with a film-forming coating which surrounds the matrix core, the composition of which
   (i) comprises at least one hydrophobic pharmaceutical film former and furthermore
   (ii) optionally pharmaceutical softeners and/or pore-forming agents and/or a hydrophilic polymer.

The active substance, e.g. the estrone sulfate and/or also other hormone constituents, can be released from the matrix film tablets according to the invention in controlled manner over 8 to 12 hours with a significant delay in the first 2 hours, the release kinetics optionally being able to be further controlled by an osmotic agent contained in the matrix.

Matrix film tablets within the scope of the present invention are understood to mean matrix tablets which have a matrix core covered with a film coating. Matrix tablets are what are called "structured tablets", which contain the active substance embedded in a polymer or wax structure or matrix. The auxiliaries used in matrix tablets, such as polymers, do not immediately dissolve in aqueous media or are not immediately eroded, so that the active substances incorporated in the matrix are not immediately released, but are released during the course of delayed erosion or slow dissolving-off of the polymeric matrix-forming auxiliary. Tablets and matrix tablets and the production thereof are familiar to the person skilled in the art of pharmaceuticals (see e.g. K. H. Bauer et al., Pharmazeutische Technologie, 1986 Thieme-Verlag, pp. 374-390). Matrix tablets and matrix cores are usually, like tablets, generally compressed in tabletting devices. Matrix tablets or matrix cores regularly contain further conventional pharmaceutical tabletting auxiliaries in addition to the matrix former responsible for the delayed release. Such auxiliaries, which are usually used for tabletting, comprise e.g. fillers, binding agents or adhesives, e.g. in the case of prior moist granulation, dry binding agents in the case of prior dry granulation, and in the case of direct tabletting, optionally humectants, drying agents or adsorbents, lubricants such as sliding agents, glidants or mould lubricants, and optionally further auxiliaries with other or additional functions. Polymers which can cause a delayed release of the active substance can also be used as dry binding agents. In addition to normal tabletting, in which binding agents are regularly used, e.g. for prior granulation, direct tabletting is also customary in pharmaceutical technology, e.g. if self-binding support materials are used. In direct tabletting, a granulation step is dispensed with and the individual supports and auxiliaries are compressed directly with the active substance.

The support materials which are suitable within the scope of the present invention must therefore meet some basic requirements, for example they must form a matrix for embedding the active substance and be suitable for tabletting, optionally for direct tabletting.

Many gel-forming pharmaceutical polymeric support materials which are suitable for tabletting, for example direct tabletting, fall within the scope of the present invention. Support materials and auxiliaries for the tablet core used within the scope of the present invention are e.g. microcrystalline cellulose, lactose, sodium chloride, magnesium stearate, optionally calcium triphosphate, polymers such as hydroxypropylcellulose, and if a granulation step is interposed, hydroxypropylmethyl celluloses. In advantageous embodiments of the present invention, the matrix film tablet is distinguished by the selection of gel-forming pharmaceutical polymeric support materials from the group of cellulose derivatives, preferably from the group of hydroxypropyl cellulose (HPC), hydroxypropylmethyl cellulose (HPMC) and/or carboxymethyl cellulose (CMC).

Furthermore, in addition to the gel-forming pharmaceutical polymeric support material many further conventional galenic auxiliaries are considered within the scope of the present invention for tablet production, in particular further auxiliaries for tabletting, for example direct tabletting. Such auxiliaries may be contained in the matrix tablet e.g. to deliberately vary the tablet properties—e.g. active-substance release characteristics, strength of the tablet or modification of the processability of the mixture to be compressed. The additional auxiliaries may therefore be e.g. further support materials—even non-matrix-forming support materials, water-soluble osmotic agent or lubricants.

In one advantageous embodiment of the matrix film tablet according to the invention, the matrix core comprises at least one gel-forming pharmaceutical polymeric support material from the group of cellulose derivatives and as further auxiliaries at least one microcrystalline cellulose as additional support material and lactose as water-soluble agent and sodium chloride as osmotic agent. The amount-related composition of preferred matrix cores of this variant of the invention is characterized in that the water-swellable matrix contains 20 to 50 parts by weight of a gel-forming pharmaceutical polymeric support material from the group of cellulose derivatives and as further pharmaceutical auxiliaries 10 to 30 parts by weight of a microcrystalline cellulose and 40 to 70 parts by weight of a water-soluble osmotic agent. Those matrix film tablets according to the invention in which the water-swellable matrix contains 20 to 50 parts by weight hydroxypropyl cellulose (HPC) as gel-forming pharmaceutical polymeric support material and as further pharmaceutical auxiliaries 10 to 30 parts by weight microcrystalline cellulose and 40 to 70 parts by weight lactose as water-soluble agent and 0.1 to 3 parts by weight sodium chloride as osmotic agent are preferred in this case.

Within the context of the present invention, in certain variants it may be advantageous if the matrix film tablet in addition to the matrix-forming support materials and optionally any other auxiliaries contains a lubricant as further auxiliary in the matrix core. The person skilled in the art is familiar with lubricants suitable for producing tablets. Examples are stearates. Preferably in the context of the present invention magnesium stearate is used as lubricant. The lubricant in the matrix film tablet according to the invention may be contained in the matrix core in an amount which relative to 100 parts by weight of the water-swellable matrix corresponds to 0.1 to 5 parts by weight, preferably 2 to 5 parts by weight.

A natural mixture of conjugated estrogens which have been obtained from pregnant mares' urine is contained as active substance constituent in the matrix film tablet according to the invention. Such natural mixtures of conjugated estrogens usually contain a number of hormones, which are present in different concentrations. Usually 17-α-estradiol, 17-β-estradiol, 17-α-DH-equilin, 17-β-DH-equilin, 17-α-DH-equilenin, 17-β-DH-equilenin, estrone, equilin, δ-8,9-dehydroestrone and equilenin may be contained as hormones in these natural mixtures. The essential hormone constituents in this case are 17-α-estradiol, 17-α-DH-equilin, 17-β-DH-equilin, estrone and equilin, wherein in particular estrone and equilin in terms of amounts form the two main constituents of the natural mixture of conjugated estrogens. The conjugated estrogens in the matrix film tablet according to the invention are preferably present in an active substance content calculated relative to the entire matrix film tablet (i.e. including the film coating described further below) as 100% by weight and as dry matter of the mixture of natural conjugated estrogens, which lies in the conventional range for pharmaceutical preparations with conjugated equine estrogens. The matrix film tablet according to the invention may alternatively or additionally to the above dry-matter content also be characterized by its total hormone content.

In an advantageous manner in accordance with the invention, the aforementioned natural mixtures of the conjugated estrogens are not incorporated directly, e.g. not directly from a CE-containing solution extract, into the water-swellable polymeric matrix-forming support material, but in the form of a preformulated homogeneous dry extract on a pharmaceutical support material. The natural mixture of the conjugated estrogens is thus present on a separate support material as dry extract or solid preformulation, via which it is virtually indirectly embedded homogeneously in the matrix. Advantageous embodiments of the matrix film tablet according to the invention are therefore distinguished by their content, relative to the matrix core, of active substance-containing preformulation, this content, in particular taking into account the active-substance content in the preformulation, possibly varying within wide ranges. The homogeneous dry extract contained in the matrix core as active substance constituent is in particular a natural mixture of conjugated estrogens preformulated on the pharmaceutical support material in a homogeneous distribution by spraying from an aqueous solution on to an originally powdery or granular pharmaceutical support material from the group of microcrystalline celluloses or a mixture of microcrystalline cellulose with lactose, and drying. Further details of the active substance-containing preformulations are given further below in conjunction with the method according to the invention for the production of the matrix film tablets.

The matrix film tablets according to the invention are furthermore characterized in that they have a film coating, i.e. a coating surrounding the matrix core. According to the invention, the coating is formed of a film composition which of necessity comprises at least one hydrophobic pharmaceutical film former and optionally furthermore pharmaceutical softeners and/or pore-forming agents.

Advantageous hydrophobic pharmaceutical film formers within the scope of the present invention are in particular those which are poorly water-soluble and which permit dissolving-off of the film by addition of hydrophilic additives or pore formers. Examples of such hydrophobic pharmaceutical film formers are polymethacrylates or polymethacrylate derivatives. The preferred hydrophobic pharmaceutical film former within the scope of the present invention is polymethacrylate.

Advantageous softeners within the scope of the present invention are in particular those which improve the plasticity of the film and make the film water-repellent or act as pore-forming agents.

One example and the preferred softener within the scope of the present invention is triethyl citrate.

Advantageous pore-forming agents within the scope of the present invention are in particular those which are readily partially dissolved or dissolved by water or aqueous media and produce pores by this dissolving out of the film. Examples of such pore-forming agents are polyethylene glycols of the types 6000 (PEG 6000) or pore-forming agents of the type hydroxypropylmethyl cellulose (HPMC). These pore-forming agents are preferred within the scope of the present invention.

In a preferred configuration of the matrix film tablets according to the invention, the latter are distinguished in that the coating comprises a polymethacrylate as hydrophobic pharmaceutical film former, e.g. triethyl citrate as softener and polyethylene glycol 6000 (PEG 6000) and/or HPMC as pore-forming agents, and also optionally talcum. In this variant the coating contains, relative to the matrix core as 100% by weight, for example the polymethacrylate in an amount of from 0.1 to 1% by weight, the triethyl citrate in an amount of from 0.05 to 0.5% by weight and polyethylene glycol 6000 in an amount of from 0.01 to 0.5% by weight and/or hydroxypropylmethyl cellulose in an amount of from 0.01 to 0.5% by weight.

According to the invention, the matrix film tablets may exist in various tablet strengths. Matrix film tablets which, including coating, have a tablet strength with a total weight of 0.3 mg, 0.625 mg, 0.9 mg, 1.25 mg or 2.5 mg in particular are advantageous. The matrix film tablets according to the invention may then, depending on tablet strength, may have different release profiles for the natural mixture of conjugated estrogens contained as active substance. In one variant of the invention, the matrix film tablet according to the invention, for the tablet strengths of 0.3 mg and 0.625 mg, has a release profile with an active-substance release, measured as the total of estrone and equilin, of 19 to 49% in 2 hours, 66 to 96% in 5 hours and >80% after 8 hours. In a further variant of the invention, the matrix film tablet according to the invention, for the tablet strengths of 0.9 mg and 0.625 mg, has a release profile with an active-substance release, measured as the total of estrone and equilin, of 12 to 37% in 2 hours, 57 to 85% in 5 hours and >80% after 8 hours. In another variant of the invention, the matrix film tablet according to the invention, for the tablet strengths of 1.25 mg and 2.5 mg, has a release profile with an active-substance release, measured as the total of estrone and equilin, of 3 to 22% in 2 hours, 37 to 67% in 5 hours, 6 to 96% in 8 hours and >80% after 12 hours.

Furthermore, the matrix film tablets according to the invention may if desired additionally have a conventional sugar coating. The sugar coating serves to seal the tablet off from air and humidity. The sugar coating may be applied in a conventional amount to the matrix film tablets, i.e. in an amount which is sufficient to fulfil the above purpose.

The present invention also relates to a method for the production of the matrix film tablet according to the invention described above. This method for the production of the matrix film tablet according to the invention described is characterized in that (a) as active substance a natural mixture of conjugated equine estrogens which is present in the form of a pharmaceutically preformulated homogeneous dry extract, the dry extract containing a standardized active-substance content (relative to the main hormone constituents) of the mixture of natural conjugated equine estrogens defined per amount of support material, and the active-substance content has been applied by spraying from an aqueous solution on to a powdery and/or granular pharmaceutical support material from the group of microcrystalline celluloses or a mixture of microcrystalline cellulose with lactose, and drying, and at least one gel-forming pharmaceutical polymeric support material from the group of cellulose and/or starch derivatives and also optionally one or more further pharmaceutical auxiliaries from the group of additional support materials in the form of microcrystalline celluloses, water-soluble osmotic agents and optionally binding agents and/or lubricants are mixed together simultaneously or in any desired sequence, if desired also with the addition of a polymer solution, preferably a hydroxypropylmethyl cellulose solution or a hydroxypropylmethyl cellulose sol, (b) the mixture obtained under (a), which has optionally already been granulated is subsequently compressed in a tabletting machine to form matrix cores, and
(c) the matrix cores obtained under (b) are coated with a coating consisting of a film composition which comprises at least one hydrophobic pharmaceutical film former and furthermore optionally a pharmaceutical softener and/or pore-forming agent.

The matrix tablets or the matrix tablet cores according to the invention are produced by mixing the support materials and auxiliaries together with the hormone-containing active substance in a suitable mixer and optionally granulating them in a suitable apparatus, e.g. with the addition of polymer such as HPMC (as solution or sol, e.g. 1-5% by weight). The granules are mixed with the suitable amount of lubricant in a suitable mixer and then compressed on a suitable tabletting machine.

Within the scope of the method according to the invention for the production of the matrix film tablet according to the invention, advantageously dry extracts which contain the natural mixture of conjugated estrogens as homogeneously distributed active substance constituent on solid support materials are used as preformulations, and which will be described further below.

The present invention uses a pharmaceutical preformulation in the form of a solid, free-flowing dry extract for tabletting, which is characterized by
(a) a standardized active-substance content (relative to the main hormone constituents) of a mixture of natural conjugated equine estrogens defined per amount of support material, wherein
(b) the active-substance content is applied by spraying from an aqueous solution on to a powdery and/or granular pharmaceutical support material from the group of microcrystalline celluloses or a mixture of microcrystalline cellulose with lactose and drying.

Conjugated equine estrogens are a mixture of various conjugated forms of estrogens which are obtained from pregnant mares' urine. The two principal main constituents are sodium estrone sulfate and sodium equilin sulfate. A third essential constituent is 17-α-dihydroequilin sulfate. In addition, sodium-17-α-estradiol sulfate and sodium-17-β-dihydroequilin sulfate are also of significance. Conjugated estrogens (CE) usually contain 52.5 to 61.5% by weight sodium estrone sulfate, 22.5 to 30.5% by weight sodium equilin sulfate, 13.5 to 19.5% by weight sodium-17-α-dihydroequilin sulfate, 2.5 to 9.5% by weight sodium-17-α-estradiol sulfate and 0.5 to 4% by weight sodium-17-β-dihydroequilin sulfate. The total proportion of sodium estrone sulfate and sodium equilin sulfate is usually in the range of 79.5 to 88% by weight. The total content of free estrogens such as estrone, equilin and 17-α-dihydroequilin is usually no more than 1.3% by weight. The above percentages relate to what is called the "labelled content", as can usually be determined and calculated in accordance with European Pharmacopoeia 2001 or analogously to USP (United States Pharmacopoeia) by means of gas-chromatographic profiles, compared with reference solutions.

The active-substance content of the hormones contained in the mixture of natural conjugated equine estrogens is usually standardized to the main hormone constituents, in which case as a rule it is geared to the total of the three main constituents estrone, equilin and 17-α-dihydroequilin, but occasionally also to the total of these three main constituents and additionally 17-α-estradiol and 17-β-dihydroequilin (in each case conjugated and free hormones).

In advantageous embodiments of the present invention, the pharmaceutical preformulation is distinguished in that the active-substance content calculated as dry matter (DM) of an extract containing the mixture of natural conjugated equine estrogens from pregnant mares' urine (total hormone content including the free estrogens and other solids) relative to the amount of the pharmaceutical support material in the preformulation lies in the range of 0.25 to 0.70 g DM/g support material, preferably in the range of 0.28 to 0.64 g DM/g support material.

If the active-substance content (total hormone content including the free estrogens) of the pharmaceutical preformulation is calculated as a mixture of natural equine conjugated estrogens (CE) relative to the amount of the pharmaceutical support material in the preformulation, the active-substance content lies in the range of 35 to 100 mg CE/g support material, preferably in the range of 43 to 90 mg CE/g support material.

After drying the pharmaceutical preformulation obtained by spraying the CE-active-substance content from an aqueous solution on to the powdery and/or granular pharmaceutical support material from the group of microcrystalline celluloses or on to a mixture of at least one of these microcrystalline celluloses with lactose, this may, due to the way it is produced, still contain a small amount of residual moisture. Usually the residual moisture content in this case lies within the scope of the usual maximum values for the drying processes used. Thus the residual moisture in the pharmaceutical preformulation is in particular at most about 3.0% by weight, preferably at most about 1.0% by weight, relative to the total preformulation as 100% by weight (total of the active-substance content calculated as dry matter, the pharmaceutical support material and taking into account the proportion of residual moisture).

If the active-substance content of the pharmaceutical preformulation used according to the invention is calculated as total hormone content (total of all conjugated and free hormones), then the active-substance content lies in the range of about 35 to 100 mg per 1 g of the pharmaceutical support material, preferably in the range of about 43 to 90 mg per 1 g of the pharmaceutical support material.

Advantageous embodiments of the pharmaceutical preformulation used according to the invention are distinguished in that the conjugated hormones (in each case as sodium salt of the sulfate ester), in particular the conjugated main hormones, are contained in the active-substance content in the following proportions: 52.5 to 61.5% estrone, 22.5 to 30.5% equilin, 13.5 to 19.5% 17-α-dihydroequilin, 2.5 to 9.5% estradiol, 0.5 to 4.0% 17-β-dihydroequilin.

Furthermore, in advantageous variants of the pharmaceutical preformulation used according to the invention the total proportion of free hormones in the preformulation lies in the range of at most about 2 to 3 mg per 1 g of the pharmaceutical support material. Preferably the proportion of free hormones in the active-substance content of the preformulation relative to the total content of hormones (total of all conjugated and free hormones) is below 5% by weight. Depending on the working-up of the hormone-containing aqueous solution extract used for the production of the pharmaceutical preformulation used according to the invention, the proportion of free hormones relative to the total hormone content may also be considerably lower, e.g. below 2% by weight.

It has surprisingly been demonstrated that by spraying a CE-solution extract obtained from PMU on to certain pharmaceutical support materials, such as microcrystalline celluloses or mixtures of these microcrystalline celluloses with lactose, by the fluidized-bed technique, the conjugated hormones can be homogeneously applied to these support materials and that the solid, free-flowing dry extract obtained thereby is advantageously suitable for producing solid galenic forms, such as tablets. In particular, the pharmaceutical preformulations used according to the invention may be distributed and compressed in the form of the dry extract homogeneously into a tablet, preferably into a matrix tablet, it being possible to achieve desired release profiles. Surprisingly, it was also shown that by selecting the pharmaceutical support material as a function of the solubility in water of the support material or support material mixture the release rate of conjugated hormones present in compressed form in a matrix tablet can be advantageously influenced. In that case, in particular the type and composition of the pharmaceutical support material or support material mixture, e.g. the type and the properties of microcrystalline cellulose and lactose, the particle size and the porosity of the active-substance granules and the particle-size distribution advantageously influence the quality of the compressibility of the resulting pharmaceutical preformulation and as a result the release profile of the conjugated hormones from a matrix tablet produced by means of this pharmaceutical preformulation. Furthermore, in addition to the above-mentioned selected pharmaceutical support materials or support material mixtures, small quantities of further conventional tabletting auxiliaries or stabilisers may be present in small quantities in the pharmaceutical preformulation used according to the invention, which makes possible further influencing of the release profile of the hormones and their stability in the pharmaceutical preformulation or solid pharmaceutical preparations produced therefrom such as tablets, in particular matrix tablets. Such tabletting auxiliaries are e.g. fillers, disintegrating agents, decomposition promoters or accelerators, dry binding agents, drying agents or adsorbents, lubricants (e.g. sliding agents, glidants or mould lubricants). These tabletting auxiliaries which have been named by way of example, or also further auxiliaries known to the person skilled in the art and usually used in tablet production, may be admixed to the preformulations used according to the invention at most in those quantities in which they are also intended to be present in the finished matrix tablet.

The successful usability of the preformulation used according to the invention for the production of solid galenic forms of natural mixtures of conjugated equine estrogen, in particular e.g. of tablets or preferably matrix tablets, is an important partial step in the production of the actual solid galenic form for therapeutic or prophylactic administration to patients, and is based, in addition to other factors, also on the type of powdery and/or granular pharmaceutical support materials selected, namely in particular pharmaceutical support materials from the group of microcrystalline celluloses and lactose, used optionally in a mixture with microcrystalline cellulose. If the pharmaceutical support material in the pharmaceutical preformulation used according to the invention is a microcrystalline cellulose, this may be a single type of microcrystalline cellulose or alternatively a mixture of different types of microcrystalline celluloses. Another variant of the invention contains mixtures of microcrystalline cellulose with lactose, which are each present in powdery and/or granular form. In the variant of the preformulations used according to the invention, in which mixtures of a microcrystalline cellulose with lactose are present as support material, the mixture ratio thereof may be varied within wide ranges, however advantageously care should be taken that the amount of the microcrystalline cellulose should not be below 60% by weight, preferably not below 80% by weight, and the amount of the lactose should not be above 40% by weight, preferably not above 20% by weight. Advantageous mixture ratios of microcrystalline cellulose to lactose are yielded if the weight ratio of microcrystalline cellulose to lactose lies in the range of 8:2 to 6:4, preferably in the range of 7.5:2.5 to 6.5:3.5. In an embodiment by way of example of the preformulation used according to the invention, the mixture ratio of microcrystalline cellulose to lactose is about 7:3 as a weight ratio.

Microcrystalline celluloses are commercially available as pharmaceutical base material in various forms, e.g. as Avicel® (e.g. from Lehmann & Voss & Co., Hamburg, Germany), in particular as Avicel® types PH 101, PH 102, PH 102 SCG or PH 103. The microcrystalline celluloses for pharmaceutical purposes commercially available as Avicel® usually have e.g. the following general specification: water content below 5% by weight (type PH 103: below 3% by weight); ash below 10; refractive index 1.55; pH (dispersion) 5.5 to 7.0; average grain sizes for

| Type | PH 101 | PH 102 | PH 102 SCG | PH 103 |
|---|---|---|---|---|
|  | 50 µm | 100 µm | 130 µm | 50 µm; | and a particle size distribution of:

| Type | PH 101 | PH 102 | PH 102 SCG | PH 103 |
|---|---|---|---|---|
| 250 µm | <1% | <8% | <8% | <1% |
| 150 µm |  |  | >23% |  |
| 75 µm | <30% | >45% | >63% | <30% |

A further commercially available microcrystalline cellulose for pharmaceutical purposes usable according to the invention is sold under the trade name Vivapur®, e.g. as type Vivapur® 101 or Vivapur® 12, (e.g. by J. Rettenmaier & Söhne GmbH+Co, Rosenberg, Germany). Vivapur® 101 usually has e.g. the following general specification: loss on drying at most 6% by weight; degree of polymerisation (identity) <350; bulk density 0.26 to 0.32 g/ml; grain size distribution: $d_{10}$: <30 µm, $d_{50}$: 40 to 70 µm, $d_{90}$: >80 µm; sieve analysis (residue on the air-jet sieve): >250 µm at most 1% by weight, >75 µm at most 30% by weight, >32 µm at least 50% by weight; pH 5.0 to 7.0; sulfate ash at most 0.05% by weight. Vivapur® 12 usually has e.g. the following general specification: loss on drying at most 6% by weight; bulk density about 0.35 g/ml; ramming volume about 1.9 ml/g; average grain size 160 µm; grain size distribution: $d_{10}$: <30 µm, $d_{50}$: 40 to 70 λm, $d_{90}$: >80 µm; sieve analysis (residue on the air-jet sieve): 400 µm at most 1% by weight, >160 µm at most 50% by weight, >50 µm at least 70% by weight.

Lactose is likewise commercially available as a pharmaceutical base material as a white, sieved, crystalline, odourless powder which is readily soluble in water and practically insoluble in ethanol, e.g. as Capsulac® (from Meggle), in particular as Capsulac® 60 or Capsulac® 200. The lactose for pharmaceutical purposes commercially available as Capsulac® 60 usually has the following specification: acid- or alkaline-reacting substances at most 0.4 ml 0.1 n sodium hydroxide solution; specific rotation 54.4° to 55.9°; water (German Pharmacopoeia) 4.5 to 5.5%; loss on drying at most 0.5% by weight; sulfate ash at most 0.1% by weight; residue on ignition at most 0.1% by weight; grain size distribution (vibratory sieving, 25 g, 10 minutes): <100 µm at most 10% by weight, <630 µm at most 97% by weight. The lactose for pharmaceutical purposes commercially available as Capsulac® 200

(type EP D 80) usually has the following specification: acid- or alkaline-reacting substances at most 0.19 ml 0.1 n sodium hydroxide solution; specific rotation 55.4°; total water 5.39% by weight; loss on drying 0.17% by weight; sulfate ash 0.04% by weight; residue on ignition 0.04% by weight; grain-size distribution (air-jet sieving, 10 g, 2 minutes): <32 μm 45 to 75% by weight, >100 μm at least 90% by weight.

In advantageous embodiments, the preformulations used according to the invention may be characterized by further parameters, such as the particle-size distribution, the mean or average particle size, the porosity of the particles, the mean apparent density (bulk density) and/or mean bulk volume.

Advantageous pharmaceutical preformulations usable according to the invention have e.g. a mean bulk volume in the range of 1.8 to 3.0 ml/g. The average apparent density (bulk density) of the pharmaceutical preformulation used according to the invention lies e.g. in the range of 0.3 to 0.6 g/ml. In one alternative, the pharmaceutical preformulation used according to the invention is distinguished in that the preformulation has a particle-size distribution characterized by sieve analysis as a percentage throughput total as a function of the sieve mesh size of 100% by weight of the particles for a mesh size of 500 μm, of at least 98% by weight of the particles for a mesh size of 250 μm, of about 65 to 99.5% by weight of the particles for a mesh size of 160 μm, of about 35 to 87% by weight of the particles for a mesh size of 125 μm, and fines of less than 23% by weight for a mesh size of 63 μm, in each case relative to the overall total of the sieve fractions as 100% by weight. Alternatively, the pharmaceutical preformulation used according to the invention is distinguished in that the preformulation has a particle-size distribution characterized by sieve analysis as a function of the sieve mesh size of approximately 0.15 to at most 2% by weight of the particles larger than a mesh size of 250 μm, of approximately 3 to 31% by weight of the particles larger than a mesh size of 160 μm, of approximately 8 to 36% by weight of the particles larger than a mesh size of 125 μm and fines of the particles of about 3 to at most 23% by weight for a mesh size of 63 μm, in each case relative to the overall total of the sieve fractions as 100% by weight. The mean (average) particle size of the pharmaceutical preformulation used according to the invention advantageously lies in the range of 50 to 250 μm, preferably in the range of 75 to 150 μm.

The present invention furthermore also describes a method for the production of the dry extracts of natural mixtures of conjugated equine estrogens used according to the invention as described above, in particular of mixtures of conjugated estrogens obtained from pregnant mares' urine, wherein pharmaceutical preformulations of natural mixtures of conjugated estrogens are provided by these dry extracts, which preformulations are suitable for the production of solid galenic forms, e.g. for the production of tablets and in particular also if desired also for direct tabletting. The method for the production of the pharmaceutical preformulation used according to the invention in the form of a solid, free-flowing dry extract of the type defined above for tabletting is distinguished in that an aqueous solution which contains a mixture of natural conjugated equine estrogens as active substance is sprayed in an amount which corresponds to the defined standardized (relative to the main hormone constituents) active-substance content desired in the pharmaceutical preformulation on to a powdery and/or granular pharmaceutical support material, fluidized in a fluidized-bed apparatus, which is selected from the group of microcrystalline celluloses or a mixture of microcrystalline cellulose with lactose, and the resulting particles containing active substance are dried.

The microcrystalline cellulose types and lactose types usable in the method have already been described further above in conjunction with the pharmaceutical preformulations used according to the invention.

For the method according to the invention, a CE-containing aqueous solution extract obtained from PMU of any origin can be used in a wide range of varying CE concentration, which can be obtained by the working-up method for the PMU described further above in relation to the prior art, in particular by the method described in U.S. Pat. No. 5,723,454 or similar methods using semipolar, preferably non-ionic semipolar adsorption resins. Depending on the concentration of the CE and the accompanying substances possibly remaining in these extracts, these aqueous extracts may be concentrated by further removal of solvent or be set to desired active-substance contents for use in the present method for the production of the dry extracts used by the addition of further water or of water-miscible organic solvents such as lower aliphatic alcohols.

In one variant of the method for obtaining the dry extracts, the active-substance-containing aqueous solution used may thus, in addition to the water, also contain other water-miscible organic solvents, in particular one or more lower aliphatic alcohols, as additional solvent. Suitable lower aliphatic alcohols are in particular those having one to four carbon atoms, for example methanol, ethanol, isopropanol or n-butanol. Methanol, ethanol or isopropanol are preferred. The organic solvents, in particular the alcohols, may also be added to the aqueous solution in a mixture with one another as additional solvent. The amount of the water-miscible organic solvent proportion, in particular the alcohol proportion, in the aqueous solution may lie in the ranges described as suitable in U.S. Pat. No. 5,723,454. Other possibly suitable water-miscible solvents such as ketones or water-soluble ethers are likewise described in U.S. Pat. No. 5,723,454.

Preferably in the method for the production of the dry extracts used aqueous solutions containing active substance, i.e. CE extract solutions or concentrates, are used which are an aqueous solution largely freed from organic solvent and suitable for galenic further processing, i.e. an essentially aqueous solution, of the CE or a concentrate of the CE largely freed of organic solvent. Purely aqueous solutions or concentrates of the natural mixture of conjugated estrogens are very much preferred in this case.

Advantageous variant embodiments of the present method for the production of the dry extracts used are distinguished in that the aqueous solution used has an active-substance content calculated as dry matter of the mixture of natural equine conjugated estrogens (total hormone content including the free estrogens and other solids) in the range of approximately 3.5 to 20% by weight relative to the aqueous solution as 100% by weight. Preferably the active-substance content in the aqueous solution calculated as dry matter of the natural mixture of conjugated equine estrogens lies in the range from approximately 3.5 to 14.5% by weight, relative to the aqueous solution as 100% by weight. If the active-substance content of the aqueous solution used in the method for the production of the dry extracts is calculated as total hormone content (including the free estrogens), the aqueous solution used has an active-substance content in the range of 10 to 100 mg per 1 g of the aqueous solution, preferably in the range of 10 to 40 mg per 1 g of the aqueous solution.

If in the method for the production of the dry extracts a concentrate is used as aqueous solution, this will advantageously have an active-substance content calculated as dry matter of the mixture of natural conjugated equine estrogens (total hormone content including the free estrogens and other solids) in the range of more than 20% by weight, relative to the concentrate as 100% by weight. If the active-substance content of the aqueous concentrate used in the method for the production of the dry extracts is calculated as total hormone content (including the free estrogens) of the mixture of natural equine conjugated estrogens (CE), the concentrate used advantageously has an active-substance content of greater than 40 mg per 1 g of the concentrate (100% by weight).

Advantageously, aqueous solutions in which the total hormone content (including the free estrogens) relative to the dry matter contained in the aqueous solution as 100% by weight lies in the range of 18 to 31% by weight are used in the method for the production of the dry extracts.

The method for the production of the dry extracts or preformulations of natural mixtures of conjugated estrogens used according to the invention, in particular of mixtures of conjugated estrogens obtained from pregnant mares' urine, can be carried out in any conventional fluidized-bed drying apparatus, in particular those for use in the pharmaceutical industry. Suitable fluidized-bed apparatus are e.g. the fluidized-bed apparatus "Strea I". In the method for the production of the dry extracts, the powdery or granular pharmaceutical support material, e.g. the microcrystalline cellulose or a mixture of microcrystalline cellulose with lactose, is placed in the fluidized-bed apparatus in a pre-calculated production amount and fluidized by means of an air current. Then an aqueous solution containing a natural mixture of conjugated estrogens as active substance in an amount which corresponds to the active-substance content desired in the preformulation is sprayed on to the support material and the resulting particles containing active substance are dried.

The method in this case may be performed both continuously and discontinuously in batch operation and in addition to the type and amount of the support material used or in addition to the type, amount and the active-substance content of the aqueous solution used, may furthermore be controlled via method parameters familiar to the person skilled in the art in the field of fluidized beds, such as incoming and exhaust air temperatures, amount of the air current supplied and withdrawn, the spraying rate of the aqueous solution and also, in the case of a continuous procedure, by the rate of introduction of the solids and discharge of product and/or the residence time of the product in the fluidized-bed apparatus.

In an advantageous variant of the method for the production of the dry extracts, e.g. the temperature, regulated using the exhaust air temperature, of the preformulation product fluidized in the fluidized-bed apparatus lies in the range of 25 to 60° C., preferably in the range of 45 to 55° C. In an example of embodiment of the method for the production of the dry extracts, e.g. the temperature, regulated using the exhaust air temperature, of the preformulation product fluidized in the fluidized-bed apparatus is approximately 45 to 55° C.

In an advantageous variant of the method for the production of the dry extracts, e.g. the process moisture regulated via the relative humidity of the exhaust air in the fluidized-bed apparatus lies in the range of 50 to 80% r.h. (r.h.=relative humidity).

In an advantageous variant of the method for the production of the dry extracts, e.g. the aqueous solution containing active substance used is sprayed at a spraying rate of 20 to 50 g/min on to the powdery and/or granular pharmaceutical support material fluidized in the fluidized-bed apparatus.

In the method for the production of the dry extracts or preformulations of natural mixtures of conjugated estrogens used according to the invention, in particular of mixtures of conjugated estrogens obtained from pregnant mares' urine, in advantageous variant embodiments powdery and/or granular support materials are used which are characterized by certain particle properties are and thus can be used for the deliberate control of the particle properties of the dry extract or preformulation product. Suitable parameters for the particle properties of the powdery or granular support materials used, just like for the characterisation of the dry-extract or preformulation products produced on this basis are e.g. the particle-size distribution, the mean or average particle size, the porosity of the particles or the mean apparent density and also further parameters deemed advantageous by the person skilled in the art in the specific case. A few advantageous ranges of these particle parameters will be given below for orientation purposes.

In an advantageous variant of the method for the production of the dry extracts, a powdery and/or granular pharmaceutical support material, in particular a microcrystalline cellulose, is used which has a particle-size distribution characterized by sieve analysis as a percentage throughput total as a function of the sieve mesh size of 100% by weight of the particles for a mesh size of 500 µm, of at least 99% by weight of the particles for a mesh size of 250 µm, of about 85 to 95% by weight of the particles for a mesh size of 160 µm, of about 70 to 80% by weight of the particles for a mesh size of 125 µm, and fines of up to about 50% by weight for a mesh size of 63 µm, in each case relative to the overall total of the sieve fractions as 100% by weight. Particularly advantageous powdery and/or granular pharmaceutical support materials used in the method for the production of the dry extracts, in particular the microcrystalline cellulose, in this case have a mean (average) particle size in the range of 50 to 130 µm. The powdery and/or granular pharmaceutical support material used in the method, in particular the microcrystalline cellulose, has e.g. an apparent density (bulk density) in the range of approximately 25 to 35 g/ml. Furthermore, the powdery and/or granular pharmaceutical support materials used in the method, in particular the microcrystalline cellulose, are characterized in that the water content (loss on drying) is at most about 6% by weight.

According to the method for the production of the dry extracts, advantageously a starting material serving for the production of pharmaceuticals which contain the natural mixture of conjugated estrogens from PMU as active component is provided which is advantageously suited as dry extract or preformulation of excellent quality for further processing by direct tabletting.

The method for the production of the dry extracts and the preformulation used according to the invention have a number of advantages in particular also with respect to other procedures. CE-containing aqueous extracts with low hormone concentration can be processed. In contrast to what is observed with conventional spray-drying of such CE-containing extracts, in the method for the production of the dry extracts in a fluidized bed undesirable attachments, e.g. to the nozzle, are not observed. The thermal loading of the valuable hormone constituents of the aqueous extracts used is very low in the fluidized bed in the method for the production of the dry extracts. Sticky properties, e.g. agglomeration, of the CE-containing aqueous extract make themselves felt less than with other drying methods such as single-pot technology. Compared with operating methods in vacuum dryers etc., the method for the production of the dry extracts is a continuously performable method which in addition—both with continuous and with discontinuous operation—permits the application of large quantities of liquid, even without over-wetting. In the method for the production of the dry extracts, a broad range of extracts both with regard to the hormone concentration and to the concentration of accompanying substances can be processed. Because of this, the method is able to solve very well the problems which have to be overcome owing to the natural fluctuations of the PMU-starting material in full-scale practice. It was demonstrated that the conjugated hormones can be applied homogeneously to the support materials by spraying a hormone concentrate using fluidized-bed technology on to support materials used according to the invention, such as microcrystalline cellulose or optionally mixtures of microcrystalline cellulose with lactose. The preformulations produced in accordance with the method in the form of solid, free-flowing dry extracts are very stable powdery or particulate hormone-containing products, which can be homogeneously distributed in matrix tablets and compressed surprisingly well. Thus matrix tablets with a desired release profile can be produced from the pharmaceutical preformulations used according to the invention in simple manner.

The successful use according to the invention of the preformulations in tabletting, for example direct tabletting, optionally also with prior granulation (e.g. with hydroxypropylmethyl cellulose solution or sol), represents an essential contribution to the production of a suitable solid galenic form for therapeutic or prophylactic administration to patients. In this case, also the type of the powdery or granular pharmaceutical support materials for the conjugated estrogens which are selected for the production of the preformulation, namely in particular pharmaceutical support materials from the group of microcrystalline celluloses and lactose optionally used in a mixture with microcrystalline cellulose, is significant for the quality of the matrix film tablet according to the invention. In particular mixtures of microcrystalline cellulose with lactose, which are each present in powdery or granular form, are preferred as support materials for the conjugated estrogens in the preformulation. In the case of preferred mixtures consisting of a microcrystalline cellulose with lactose as support material, the mixture ratio thereof may be varied within wide ranges. Advantageous mixture ratios of microcrystalline cellulose to lactose are given above. In an embodiment by way of example of the preformulation used according to the invention for the production of matrix film tablets, the mixture ratio of microcrystalline cellulose to lactose is about 7:3 as weight ratio.

Microcrystalline celluloses are commercially available as pharmaceutical base material in various embodiments, and are described above e.g. as Avicel® or Avicel® PH 102. Lactose is likewise commercially available as pharmaceutical base material, e.g. as Capsulac®, in particular as Capsulac®60, and has likewise already been described above.

The matrix film tablets according to the invention can be produced, taking into account the above particulars and using conventional galenic procedures for the production of matrix tablet cores, e.g. by tabletting, for example direct tabletting, for the subsequent coating of the matrix tablet cores with a film coating and finally optionally for applying a sugar coating. The matrix tablet cores may be provided with the film coating by applying a suspension of e.g. polymethacrylate and/or polymethacrylate derivatives (e.g. Eudrojet, RL 30D), e.g. PEG 6000, e.g. triethyl citrate, talcum and optionally hydroxypropylmethyl cellulose to the matrix core in a suitable apparatus. Finally, additionally a sugar coating may be applied to the matrix film tablets provided with the film coating using a conventional galenic procedure.

The following examples are intended to illustrate the invention in further detail without limiting its scope.

EXAMPLES

Example 1

Drying and Production of a Preformulation with Hormone-Containing Active Substance in a Fluidized-Bed Apparatus, and Hormone Content A series of tests were carried out with the aim of developing a hormone-containing active substance by drying the hormones from urine concentrate from pregnant mares. The conjugated hormones in this case had to be put into a form which guarantees the chemical stability of the hormones and permits processing of the hormones into a tablet. A urine concentrate (concentrated aqueous solution of pregnant mares' urine=PMU) from a collecting campaign in Asia was used, which was characterized by its amount of dry matter and hormone concentration. The urine concentrate was worked up before use in accordance with the method of U.S. Pat. No. 5,723,454, in order to separate off undesirable accompanying substances such as urea, HPMF and cresols.

In the tests, it was demonstrated that the conjugated hormones could be applied homogeneously to the auxiliaries by spraying the hormone concentrate on to support materials such as microcrystalline cellulose or mixtures of microcrystalline cellulose with lactose using fluidized-bed technology.

A urine concentrate provided from a collecting campaign was sprayed on to microcrystalline cellulose or on to a mixture of microcrystalline cellulose and lactose and the hormones were thereby applied to the support or the mixture of support materials. This process was carried out in a fluidized-bed granulator. The particle size and porosity of the active-substance granules were regulated by the incoming and exhaust air temperatures and the spraying rate. The product temperature (regulated using the exhaust air temperature), which was set in the range of 25 to 55° C., and the process humidity (regulated via relative exhaust air humidity), which was set in the range of 50 to 80% relative air humidity, served as parameters for the process. The spraying rate was selected accordingly in order to maintain the aforementioned ranges.

In these tests, a fluidized-bed apparatus (Strea 1) was used for the production of dry extracts of natural mixtures of conjugated estrogens, with which about 1 kg dry extract per batch can be produced. The aqueous solution extract containing a natural mixture of conjugated estrogens was introduced into the fluidized-bed apparatus using the top-spray method. The further industrial equipment comprised:
  Sartorius balance/6.2 kg/type LC6200S-OD2,
  tubing pump Masterflex 07523-27 with pump head 7518-10,
  moisture measuring apparatus of the type HR 73 from Mettler Toledo.

The tests in the fluidized-bed apparatus were carried out with aqueous solution extracts containing a natural mixture of conjugated estrogens which came from a collecting campaign in Asia which was worked up in accordance with the method described in U.S. Pat. No. 5,723,454, the hormone-containing aqueous extracts having the following hormone contents:
Test 1: DM=9.2% by weight
Test 2: DM=15.9% by weight
Test 3: DM=19.3% by weight
Test 4: DM=9.2% by weight
In further tests, CE-containing aqueous solution extracts with DM=11.8% by weight (Test 5) or DM=9.9% by weight (Test 6) were used. The aqueous solution extracts all had a crystalline or oily deposit, which impaired homogeneous processing, but not substantially. The aqueous solution extracts had only a relatively low hormone content, which is why the dry extracts were set to a theoretical desired content of 45 mg conjugated estrogens per g dry extract.

There were used as support materials for the natural mixture of conjugated estrogens:

Avicel PH 102,

Capsulac 60.

Performance of the Tests

Production of a dry extract with a content of 45 mg conjugated estrogens per g dry extract for receiving solutions of 570 to 680 g of the support material.

| Test 1: | |
| --- | --- |
| Extract used: | 4023.1 g; DM = 9.2% by weight; Density: 1.0365 g/l; CE = 12.14 g/l |
| Receiving solution: | 677.0 g Avicel PH 102 |
| Spraying rate: | 40-50 g/min (approximate mean value) |
| Relative exhaust air humidity: | 70-80% |
| Exhaust air temperature: | 32-34° C. |

| Test 2: | |
| --- | --- |
| Extract used: | 2400.0 g; DM = 15.9% by weight; |
| Density: | 1.0662 g/l; CE = 20.86 g/l |
| Receiving solution: | 661.9 g Avicel PH 102 |
| Spraying rate: | 40-50 g/min (approximate mean value) |
| Relative exhaust air humidity: | 70-80% |
| Exhaust air temperature: | 32-34° C. |

| Test 3: | |
| --- | --- |
| Extract used: | 1904.6 g; DM = 19.3% by weight; |
| Density: | 1.0662 g/l; CE = 20.86 g/l |
| Receiving solution: | 574.8 g Avicel PH 102 |
| Spraying rate: | 40-50 g/min (approximate mean value) |
| Relative exhaust air humidity: | 70-80% |
| Exhaust air temperature: | 32-34° C. |

All three tests took place without problems. The spraying times for Test 1 were 83 minutes, for Test 2 46 minutes and for Test 3 35 minutes.

| Test 4: | |
| --- | --- |
| Extract used: | 4023.1 g; DM = 9.2% by weight; |
| Density: | 1.0365 g/l; CE = 12.14 g/l |
| Receiving solution: | 677.0 g Avicel PH 102 |
| Spraying rate: | 40-50 g/min (approximate mean value) |
| Relative exhaust air humidity: | 50-60% |
| Exhaust air temperature: | 35-40° C. |

This test is a repetition of Test 1, which is intended to check whether a finer dry extract can be produced by reducing the spraying rate. The dry extract in sieve analyses proved to be finer than the dry extract obtained in Test 1 (see summary of the results of the tests).

Further tests were carried out using analogous procedures to Tests 1 to 3 with Avicel PH 102 (Test 5) or with mixtures of Avicel PH 102 and Capsulac 60 (weight ratio 7:3; Test 6).

Test Results

Detailed results on the hormone content in Tests 1 to 4 are compiled in Tables I to IV. In principle it was discovered that, for a receiving solution of 570 g to 680 g Avicel PH 102 as support material, continuous and rapid application of the extract is possible (Tests 1 to 3). For the amounts of extract used, which varied from 1900 to 4023 g, the spraying times for these tests were between 35 and 83 minutes. This yielded applied amounts of 0.55 g to 0.64 g solids from the extract per g Avicel (mean value: 0.59 g).

In order in a further test (Test 5) to maintain the preset desired content of 45 mg conjugated estrogens per g dry extract or to determine limits for maximum quantities of active substance which can be applied, in this test the receiving solution of Avicel PH 102 was reduced to 342.5 g, compared with the previous Tests 1 to 4, i.e. a reduction of almost 50%. 4640 g extract was to be applied. In this case, for up to about 1600 g extract sprayed on no problems occurred, since up to this amount as in the preceding Tests 1 to 4 again there was an applied amount of 0.56 g solids from the extract per g Avicel. For about 2000 g extract sprayed on, an applied amount of 0.68 g was yielded, and for about 2500 g an amount of 0.86 g solids from the extract per g Avicel. Up to this applied amount, the extract could be sprayed on largely without problems. Thereafter, the spraying rate was greatly reduced, since from this amount onwards the solids from the extract exceed the amount of the support material and the product exhibits a tendency to stick from this point onwards. The process was then only operated at a relative humidity of <25%, since the exhaust-air filters clogged up; the amount of air was no longer sufficient to maintain the fluidized bed. The pure spraying time was more than 5 hours.

In summary, it can therefore be said that up to an application of 0.6 g solids from the extract per g Avicel the entire extract should be processed. The upper limit of quantities of extract which Avicel PH 102 can take without being impaired lies at about 0.86 g application of solids from the extract. Thereafter, it is necessary to reduce the spray application and to adapt the remaining parameters accordingly.

Test 4 is a repetition of Test 1. Here, a finer trituration was produced by changing the parameters (lower spraying rate and hence higher exhaust air temperature and a lower exhaust air humidity).

In the additional Test 6, as in Test 4, a reduction in the receiving solution was effected, in order to be able to set to 45 mg conjugated estrogens per g trituration (reduction >60% compared with Test 1 and Test 2). Additionally, lactose was used in this instance (ratio Avicel to lactose=7 to 3). In this test, from an applied quantity of 0.6 g solids from the extract per g Avicel/lactose mixture onwards, it was necessary to lower the spraying rate from 20 g/min to <9 g/min (at V-140 the limit was at 0.86 g solids). The amount of extract sprayed on at this moment was about 40% by weight (<1600 g). From about 1800 g onwards, here too, as already observed in Test 4, there was a tendency to stick. The test was discontinued after application of 70% amount of extract, since it was not possible to reduce the spraying rate further (<9 g/min) due to the apparatus.

TABLE I

Hormone content for Test 1

| Estrogens | Total estrogens | | | | Free estrogens | | | |
|---|---|---|---|---|---|---|---|---|
| | Solution extract | | Dry extract | | Solution extract | | Dry extract | |
| | [mg/g] | [%][1] | [mg/g] | [%][1] | [Mg/g] | [%][2] | [Mg/g] | [%][2] |
| 17-α-estradiol | 0.455 | 4.34 | 1.856 | 4.31 | 0.047 | | 0.196 | |
| 17-β-estradiol | 0.646 | 6.17 | 2.631 | 6.12 | 0.082 | | 0.344 | |
| 17-α-DH-equilin | 1.270 | 12.12 | 5.160 | 11.99 | 0.098 | 0.94 | 0.405 | 0.94 |
| 17-β-DH-equilin | 0.322 | 3.07 | 1.323 | 3.08 | 0.019 | | 0.077 | |
| 17-α-DH-equilenin | 0.057 | 0.54 | 0.229 | 0.53 | 0.007 | | 0.021 | |
| 17-β-DH-equilenin | 0.031 | 0.30 | 0.215 | 0.50 | 0.000 | | 0.000 | |
| Estrone | 6.193 | 59.12 | 25.371 | 58.97 | 0.247 | 2.36 | 1.015 | 2.36 |
| Equilin | 2.236 | 21.34 | 9.312 | 21.64 | 0.057 | 0.54 | 0.229 | 0.53 |
| δ-8,9-dehydroestrone | 0.293 | 2.80 | 1.223 | 2.84 | 0.022 | | 0.076 | |
| Equilenin | 0.124 | 1.18 | 0.515 | 1.20 | 0.000 | | 0.000 | |
| Total hormone content | 11.627 | | 47.835 | | 0.579 | | 2.363 | |
| Total main hormones[3] | 10.476 | | 43.022 | | 0.468 | | 1.922 | |

[1] relative to 17-α-estradiol, 17-α-DH-equilin, 17-β-DH-equilin, estrone and equilin
[2] relative to total of 17-α-estradiol, 17-α-DH-equilin, 17-β-DH-equilin, estrone and equilin from total estrogens
[3] total of the hormones 17-α-estradiol, 17-α-DH-equilin, 17-β-DH-equilin, estrone and equilin

TABLE II

Hormone balance for Test 2

| Estrogens | Total estrogens | | | | Free estrogens | | | |
|---|---|---|---|---|---|---|---|---|
| | Solution extract | | Dry extract | | Solution extract | | Dry extract | |
| | [Mg/g] | [%][1] | [Mg/g] | [%][1] | [Mg/g] | [%][2] | [Mg/g] | [%][2] |
| 17-α-estradiol | 0.826 | 4.46 | 2.085 | 4.49 | 0.087 | | 0223 | |
| 17-β-estradiol | 1.220 | 6.58 | 3.074 | 6.62 | 0.163 | | 0.417 | |
| 17-α-DH-equilin | 2.302 | 12.42 | 5.824 | 12.54 | 0.177 | 0.96 | 0.437 | 0.94 |
| 17-β-DH-equilin | 0.634 | 3.42 | 1.506 | 3.24 | 0.036 | | 0.087 | |
| 17-α-DH-equilenin | 0.124 | 0.57 | 0.298 | 0.64 | 0.012 | | 0.030 | |
| 17-β-DH-equilenin | 0.103 | 0.56 | 0.242 | 0.52 | 0.000 | | 0.000 | |
| Estrone | 10.835 | 58.47 | 27.056 | 58.28 | 0.423 | 2.28 | 1.056 | 2.27 |
| Equilin | 3.934 | 21.23 | 9.957 | 21.45 | 0.092 | 0.50 | 0.223 | 0.50 |
| δ-8,9-dehydroestrone | 0.529 | 2.85 | 1.348 | 2.90 | 0.016 | | 0.079 | |
| Equilenin | 0.220 | 1.19 | 0.543 | 1.17 | 0.000 | | 0.000 | |
| Total hormone content | 20.727 | | 51.933 | | 1.006 | | 2.562 | |
| Total main hormones[3] | 18.531 | | 46.428 | | 0.815 | | 2.036 | |

[1] relative to 17-α-estradiol, 17-α-DH-equilin, 17-β-DH-equilin, estrone and equilin
[2] relative to total of 17-α-estradiol, 17-α-DH-equilin, 17-β-DH-equilin, estrone and equilin from total estrogens
[3] total of the hormones 17-α-estradiol, 17-α-DH-equilin, 17-β-DH-equilin, estrone and equilin

TABLE III

Hormone content for Test 3

| Estrogens | Total estrogens | | | | Free estrogens | | | |
|---|---|---|---|---|---|---|---|---|
| | Solution extract | | Dry extract | | Solution extract | | Dry extract | |
| | [Mg/g] | [%][1] | [Mg/g] | [%][1] | [Mg/g] | [%][2] | [Mg/g] | [%][2] |
| 17-α-estradiol | 1.003 | 4.64 | 2.208 | 4.57 | 0.102 | | 0.227 | |
| 17-β-estradiol | 1.402 | 6.49 | 3.072 | 6.36 | 0.166 | | 0.365 | |
| 17-α-DH-equilin | 2.678 | 12.40 | 5.984 | 12.39 | 0.207 | 0.96 | 0.463 | 0.96 |
| 17-β-DH-equilin | 0.633 | 2.93 | 1.432 | 2.96 | 0.038 | | 0.091 | |
| 17-α-DH-equilenin | 0.118 | 0.55 | 0.232 | 0.48 | 0.021 | | 0.031 | |
| 17-β-DH-equilenin | 0.045 | 0.21 | 0.057 | 0.12 | 0.000 | | 0.000 | |

TABLE III-continued

Hormone content for Test 3

| | Total estrogens | | | | Free estrogens | | | |
| --- | --- | --- | --- | --- | --- | --- | --- | --- |
| | Solution extract | | Dry extract | | Solution extract | | Dry extract | |
| Estrogens | [Mg/g] | [%][1] | [Mg/g] | [%][1] | [Mg/g] | [%][2] | [Mg/g] | [%][2] |
| Estrone | 12.713 | 58.87 | 28.105 | 58.18 | 0.492 | 2.28 | 1.083 | 2.24 |
| Equilin | 4.569 | 21.16 | 10.582 | 21.90 | 0.107 | 0.50 | 0.241 | 0.50 |
| δ-8,9-dehydroestrone | 0.539 | 2.50 | 1.265 | 2.62 | 0.021 | | 0.113 | |
| Equilenin | 0.222 | 1.03 | 0.492 | 1.02 | 0.000 | | 0.000 | |
| total hormone content | 23.922 | | 53.429 | | 1.154 | | 2.614 | |
| Total main hormones[3] | 21.596 | | 48.311 | | 0.946 | | 2.105 | |

[1] relative to 17-α-estradiol, 17-α-DH-equilin, 17-β-DH-equilin, estrone and equilin
[2] relative to total of 17-α-estradiol, 17-α-DH-equilin, 17-β-DH-equilin, estrone and equilin from total estrogens
[3] total of the hormones 17-α-estradiol, 17-α-DH-equilin, 17-β-DH-equilin, estrone and equilin

TABLE IV

Hormone content for Test 4

| | Total estrogens | | | | Free estrogens | | | |
| --- | --- | --- | --- | --- | --- | --- | --- | --- |
| | Solution extract | | Dry extract | | Solution extract | | Dry extract | |
| Estrogens | [Mg/g] | [%][1] | [mg/g][1] | [%] | [Mg/g] | [%][2] | [Mg/g] | [%][2] |
| 17-α-estradiol | 0.646 | 4.56 | 2.284 | 4.56 | 0.057 | | 0.201 | |
| 17-β-estradiol | 1.093 | 7.71 | 3.798 | 7.58 | 0.151 | | 0.531 | |
| 17-α-DH-equilin | 1.876 | 13.23 | 6.367 | 12.71 | 0.134 | 0.94 | 0.484 | 0.97 |
| 17-β-DH-equilin | 0.523 | 3.69 | 1.768 | 3.53 | 0.018 | | 0.109 | |
| 17-α-DH-equilenin | 0.070 | 0.49 | 0.274 | 0.55 | 0.008 | | 0.030 | |
| 17-β-DH-equilenin | 0.000 | 0.00 | 0.103 | 0.21 | 0.000 | | 0.000 | |
| Estrone | 8.022 | 56.57 | 28.947 | 57.77 | 0.282 | 1.99 | 1.038 | 2.07 |
| Equilin | 3.114 | 21.96 | 10.743 | 21.44 | 0.068 | 0.50 | 0.229 | 0.46 |
| δ-8,9-dehydroestrone | 0.381 | 2.69 | 1.339 | 2.67 | 0.022 | | 0.083 | |
| Equilenin | 0.119 | 0.84 | 0.543 | 1.08 | 0.000 | | 0.000 | |
| total hormone content | 15.844 | | 56.166 | | 0.740 | | 2.705 | |
| Total main hormones[3] | 14.181 | | 50.109 | | | | 2.057 | |

[1] relative to 17-α-estradiol, 17-α-DH-equilin, 17-β-DH-equilin, estrone and equilin
[2] relative to total of 17-α-estradiol, 17-α-DH-equilin, 17-β-DH-equilin, estrone and equilin from total estrogens
[3] total of the hormones 17-α-estradiol, 17-α-DH-equilin, 17-β-DH-equilin, estrone and equilin Evaluation of the Test Results The production of a dry extract in the fluidized-bed apparatus, even with support materials of different grain-size distribution, is not problematic. The yield determined for all tests was between 90 and 95%. The hormone distribution, relative to 17-α-DH-equilin, estrone and equilin, is constant in the extract and in the trituration. The drying process therefore has no influence on the stability of the hormones. The residual moisture content was between 3 and 6% relative humidity (r.h.).

As the tests show, it is possible to process large quantities of hormone-containing extract of 2 to 4 kg within a short time, i.e. to apply it to support materials and dry it accordingly. The maximum applied amounts determined (g solids from the extract per g support material, e.g. Avicel) which can be applied to the selected support material without process problems should be emphasized as being particularly important. In this case it was established that when e.g. Avicel is used as support material an application of up to about 0.6 g active-substance dry matter from the hormone-containing aqueous solution extract per g Avicel is completely without problems (Tests 1, 2 and 3 of Example 1).

Example 2

Tabletting Tests

In order to test the galenic further processing ability of the dry extracts or preformulations produced in Example 1 by fluidized-bed technology, the dry extracts or preformulations were mixed with further tabletting auxiliaries and compressed to form matrix tablets. It was demonstrated that the mixtures could be homogeneously distributed in a matrix tablet and compressed. Surprisingly, it was demonstrated that by selecting the support material and the further tabletting auxiliaries as a function of the solubility of the support material and tabletting-auxiliary mixture in water the release rate of the conjugated hormones compressed in the matrix tablets can be decisively influenced, and that thus desired, preset release profiles can be set. Also the composition of the support material used as support for the conjugated estrogens, e.g. of the mixture of microcrystalline cellulose with lactose, the particle size and the porosity of the active-substance granules, and also the particle-size distribution influence the quality of the compressibility and the release profile of the hormones which are released from the matrix.

Example 3

Matrix Tablets with Controlled Active-Substance Release

The preferred preformulation for the production of matrix tablets consists of a dry-extract fraction described in Example 1 mixed with microcrystalline cellulose as active substance, which is granulated finely with the auxiliaries microcrystalline cellulose, lactose, hydroxypropyl cellulose type M in a fluidized-bed granulator with a hydroxypropylmethyl cellulose solution. The granules produced are then optionally mixed with NaCl and Mg stearate and then tabletted. The tablet is then if desired provided with a coating which consists of HPMC (hydroxypropylmethyl cellulose), polymethacrylate derivatives (e.g. Eudragit RL 30D), polyethylene glycols such as 6000, triethyl citrate and talcum in a suitable coater.

The aim of the film-coating of the matrix tablets is to achieve a delay in the release (control of the blood level in the body) at the start of the release curve in the form of a desired, preset lag time. The film tablet is additionally finally sugar-coated in order to guarantee sufficient stability of the hormone action.

In vitro release investigations in accordance with the USP method were carried out in demineralized water. The aim is to control the release rate in water, in order to meet the USP requirements and to set a predetermined release profile. Since it is not demineralized water but osmotically active liquids which predominate in the body and likewise different pH values are found in the stomach and intestines, continuing releases were carried out in osmotically active media and optionally also in buffer media.

It was demonstrated that for an NaCl-containing film tablet the different in the release in demineralized water compared with the release in 0.9% NaCl solution is relatively low.

By adding NaCl in the outer region of the matrix tablet, i.e. by mixing with the granules produced and Mg stearate, the drawing of water into the tablet after penetrating the film is increased. This provides a counter-force above all in osmotically active media and produces an increased swelling pressure, which in turn produces a pressure on the film. The film thus bursts open more quickly after achieving a desired lag time due to the resulting pressure and thus permits a release profile determined by the genuine tablet.

I. Matrix Film Tablets

| A. Film tablet 0.625 mg (with NaCl) | |
|---|---|
| Matrix core | amount in mg/individual dose |
| Dry extract fraction | 7.1 |
| Vivapur 101 | 7.5 |
| Vivapur 101 | 16.1 |
| Granulac 200 | 47.2 |
| HPC-M, fine | 31.2 |
| Pharmacoat type 603 | 3.4 |
| NaCl | 7.0 |
| Mg stearate | 0.5 |
| | 120.0 |

| A. Film tablet 0.625 mg (with NaCl) | |
|---|---|
| Film-coating | amount in mg/individual dose |
| PEG 6000 | 0.28 |
| Methocel E5 | 0.948 |
| Triethyl citrate | 0.56 |
| Talcum, micronised | 0.812 |
| Eudragit RL 30D | 0.9 |
| Water | — |
| | 123.5 |

| B. Film tablet 0.625 mg (without NaCl) | |
|---|---|
| Matrix core | amount in mg/individual dose |
| Dry extract fraction | 7.1 |
| Vivapur 101 | 7.5 |
| Vivapur 101 | 17.8 |
| Granulac 200 | 52.3 |
| HPC-M, fine | 31.2 |
| Pharmacoat type 603 | 3.6 |
| Mg stearate | 0.5 |
| | 120.0 |
| Film-coating | amount in mg/individual dose |
| PEG 6000 | 0.28 |
| Methocel E5 | 0.948 |
| Triethyl citrate | 0.56 |
| Talcum, micronised | 0.812 |
| Eudragit RL 30D | 0.9 |
| Water | — |
| | 123.5 |

| C. Film tablet 0.625 mg (with NaCl, film coating 1.5 mg/ID) | |
|---|---|
| Matrix core | amount in mg/individual dose |
| Dry extract fraction | 7.1 |
| Vivapur 101 | 7.5 |
| Vivapur 101 | 16.1 |
| Granulac 200 | 47.2 |
| HPC-M, fine | 31.2 |
| Pharmacoat type 603 | 3.4 |
| NaCl | 7.0 |
| Mg stearate | 0.5 |
| | 120.0 |
| Film-coating | amount in mg/individual dose |
| Eudragit RL 30D | 0.615 |
| Triethyl citrate | 0.300 |
| PEG 6000 | 0.150 |
| Talcum, micronised | 0.435 |
| Water | — |
| | 121.5 |

| D. Matrix tablet 0.625 mg (without NaCl) | |
|---|---|
| Matrix core | amount in mg/individual dose |
| Dry extract fraction | 7.1 |
| Vivapur 101 | 7.5 |
| Vivapur 101 | 17.8 |
| Granulac 200 | 52.3 |
| HPC-M, fine | 31.2 |
| Pharmacoat type 603 | 3.6 |
| Mg stearate | 0.5 |
| | 120.0 |
| Film-coating | amount in mg/individual dose |
| None | |

| E. Matrix tablet 0.625 mg (with NaCl, without film-coating) | |
|---|---|
| Matrix core | amount in mg/individual dose |
| Dry extract fraction | 7.1 |
| Vivapur 101 | 7.5 |
| Vivapur 101 | 16.1 |
| Granulac 200 | 47.2 |
| HPC-M, fine | 31.2 |
| Pharmacoat type 603 | 3.4 |
| NaCl | 7.0 |
| Mg stearate | 0.5 |
| | 120.0 |
| Film-coating | amount in mg/individual dose |
| none | |

| F. Matrix tablet 0.625 mg (with NaCl, without film-coating) | |
|---|---|
| Matrix core | amount in mg/individual dose |
| Dry extract fraction | 7.1 |
| Vivapur 101 | 7.5 |
| Vivapur 101 | 16.0 |
| Granulac 200 | 47.1 |
| HPC-M, fine | 31.2 |
| Pharmacoat type 603 | 3.6 |
| NaCl | 7.0 |
| Mg stearate | 0.5 |
| | 120.0 |
| Film-coating | amount in mg/individual dose |
| none | |

Tablet produced with NaCl, which was provided directly upon granulation as receiving solution in the mixture.

II. Active-Substance Release

| Dissolution test in 0.9%-strength NaCl solution | |
|---|---|
| Test method: | Paddle agitator |
| Speed of rotation: | 50 rpm |
| Test medium: | 0.9% NaCl |
| Test volume: | 900 ml |
| Sample volume | 10 ml |
| Tester: | Sotax AT 7 smart D 10 |
| HPLC: HPLC apparatus: | H_LC_04 |
| Column type: | LUNA 3 μm C 18(2) |

| Release of estrone: Matrix film tablet A (with NaCl) | | | | | | |
|---|---|---|---|---|---|---|
| Vessel No. | 1 | 2 | 3 | 4 | 5 | 6 |
| wt. [mg] | 122.72 | 126.29 | 124.49 | 124.97 | 124.90 | 125.23 |
| 1 | 9.352 | 8.230 | 7.397 | 9.606 | 9.321 | 9.124 |
| 2 | 27.423 | 24.591 | 22.671 | 28.323 | 24.337 | 25.889 |
| 5 | 76.696 | 63.356 | 59.298 | 75.712 | 69.859 | 63.550 |
| 8 | 100.805 | 87.565 | 80.090 | 96.837 | 89.642 | 86.569 |

| Release of estrone: Matrix film tablet B (without NaCl) | | | | | | |
|---|---|---|---|---|---|---|
| Vessel No. | 1 | 2 | 3 | 4 | 5 | 6 |
| wt. [mg] | 125.14 | 124.03 | 126.15 | 124.83 | 126.95 | 127.34 |
| 1 | 7.957 | 8.391 | 7.602 | 7.197 | 9.997 | 7.883 |
| 2 | 21.605 | 23.843 | 20.862 | 20.437 | 20.2457 | 22.347 |
| 5 | 56.943 | 66.647 | 53.262 | 54.357 | 62.641 | 57.929 |
| 8 | 80.416 | 88.703 | 76.113 | 77.485 | 86.548 | 78.929 |

| Release of estrone: Matrix film tablet C (with NaCl, coating without HPMC) | | | | | | |
|---|---|---|---|---|---|---|
| Vessel No. | 1 | 2 | 3 | 4 | 5 | 6 |
| wt. [mg] | 120.14 | 122.29 | 121.92 | 121.76 | 120.60 | 121.64 |
| 1 | 5.233 | 3.808 | 3.437 | 3.977 | 3.783 | 4.528 |
| 2 | 15.569 | 12.260 | 10.913 | 12.757 | 12.708 | 16.240 |
| 5 | 72.993 | 67.216 | 62.390 | 72.676 | 71.998 | 77.769 |
| 8 | 88.783 | 86.697 | 83.630 | 90.331 | 89.873 | 90.329 |

| Release of estrone: Matrix film tablet D (without NaCl, without coating) | | | | | | |
|---|---|---|---|---|---|---|
| Vessel No. | 1 | 2 | 3 | 4 | 5 | 6 |
| wt. [mg] | 119.63 | 120.09 | 120.55 | 120.48 | 119.71 | 121.21 |
| 1 | 34.299 | 35.517 | 35.024 | 36.913 | 34.113 | 34.618 |
| 2 | 52.663 | 53.096 | 52.718 | 56.150 | 52.136 | 52.285 |
| 5 | 89.068 | 88.165 | 86.086 | 92.987 | 87.094 | 88.125 |
| 8 | 101.905 | 100.326 | 99.713 | 103.604 | 97.611 | 102.261 |

| Release of estrone: Matrix film tablet E (with NaCl, without coating) | | | | | | |
|---|---|---|---|---|---|---|
| Vessel No. | 1 | 2 | 3 | 4 | 5 | 6 |
| wt. [mg] | 120.22 | 120.08 | 120.82 | 119.12 | 119.71 | 120.47 |
| 1 | 25.507 | 23.697 | 25.039 | 24.647 | 24.782 | 24.781 |
| 2 | 45.241 | 42.410 | 44.036 | 44.166 | 44.581 | 44.697 |

-continued

Release of estrone: Matrix film tablet E (with NaCl, without coating)

| Vessel No. wt. [mg] | 1<br>120.22 | 2<br>120.08 | 3<br>120.82 | 4<br>119.12 | 5<br>119.71 | 6<br>120.47 |
|---|---|---|---|---|---|---|
| 5 | 89.396 | 86.501 | 88.947 | 89.724 | 89.869 | 91.462 |
| 8 | 98.565 | 101.113 | 101.846 | 101.910 | 102.163 | 102.875 |

Release of estrone: Matrix film tablet F (with NaCl, without coating)

| Vessel No. wt. [mg] | 1<br>120.16 | 2<br>120.51 | 3<br>120.65 | 4<br>119.25 | 5<br>121.07 | 6<br>120.84 |
|---|---|---|---|---|---|---|
| 1 | 26.502 | 50.097 | 24.346 | 25.389 | 21.941 | 25.461 |
| 2 | 48.852 | 69.102 | 42.665 | 44.772 | 39.979 | 44.818 |
| 5 | 95.432 | 94.347 | 87.589 | 89.842 | 80.394 | 87.613 |
| 8 | 102.050 | 94.248 | 101.189 | 99.147 | 89.638 | 95.833 |

The foregoing description and examples have been set forth merely to illustrate the invention and are not intended to be limiting. Since modifications of the described embodiments incorporating the spirit and substance of the invention may occur to persons skilled in the art, inventin should be construed broadly to include all variations within the scope of the appended claims and equivalents thereof.

What is claimed is:

1. A pharmaceutical matrix film tablet with controlled active-substance release, said tablet comprising:
   (a) a water-swellable matrix core comprising,
      (i) a mixture of natural conjugated equine estrogens in the form of a pharmaceutically preformulated homogeneous dry extract, wherein the pharmaceutically preformulated homogeneous dry extract is produced by spraying an aqueous solution of a mixture of natural conjugated equine estrogens as active-substance content onto a powdered or granular pharmaceutical support material selected from the group consisting of microcrystalline celluloses and mixtures of microcrystalline cellulose with lactose, and drying; and
      wherein the pharmaceutically preformulated dry extract achieves a standardized active-substance content that is standardized with regard to the main hormone constituents, which comprise estrone, equilin and 17-α-dihydroequilin, and optionally 17-α-estradiol and 17-β-dihydroequilin, in their conjugated and free forms, and defined per amount of support material,
      wherein the active substance content defined per amount of support material is calculated as dry matter of an extract containing the natural mixture of conjugated equine estrogens from pregnant mares' urine including the free estrogens and other solids relative to the amount of the pharmaceutical support material in the pharmaceutically preformulated homogeneous dry extract, or total hormone content comprising the conjugated and the free estrogens from pregnant mares' urine relative to the amount of the pharmaceutical support material in the pharmaceutically preformulated homogeneous dry extract; and
      (ii) a water-swellable matrix comprising at least one matrix former selected from the group consisting of gel-forming pharmaceutical polymers, and also optionally one or more further pharmaceutical tabletting auxiliary substances selected from the group consisting of other matrix formers, fillers, binding agents, water-soluble osmotic agents and lubricants, wherein the gel-forming pharmaceutical polymer is present in an amount of 20 to 50 parts by weight and selected from the group consisting of hydroxypropyl cellulose (HPC) hydroxypropylmethyl cellulose (HPMC) and carboxymethyl cellulose (CMC);
         wherein the other matrix former is microcrystalline cellulose present in an amount of 10 to 30 parts by weight; and
         wherein the water-soluble agent is lactose present in an amount of 40 to 70 parts by weight; and
      wherein the water-swellable matrix core represents a tabletted mixture of the preformulated homogeneous dry extract with the water-swellable matrix; and
   (b) a film-forming coating surrounding the matrix core, said coating comprising:
      (i) at least one hydrophobic pharmaceutical film former, and
      (ii) optionally, one or more agents selected from the group consisting of pharmaceutical softeners, pore-forming agents and hydrophilic polymers;
   wherein the matrix film tablet has one of the following release profile with an active-substance release measured as the total of estrone and equilin:
      (i) 19% to 49% in 2 hours, 66% to 96% in 5 hours and greater than 80% after 8 hours; or
      (ii) 12% to 37% in 2 hours, 57% to 85% in 5 hours and greater than 80% after 8 hours; or
      (iii) 3% to 22% in 2 hours, 37% to 67% in 5 hours, 6% to 96% on 8 hours and greater than 80% after 12 hours.

2. A tablet according to claim 1, wherein the water-swellable matrix contains at least one lubricant selected from the group consisting of sliding agents, glidants and mold lubricants.

3. A tablet according to claim 1, wherein the osmotic agent is sodium chloride.

4. A tablet according to claim 1, wherein the osmotic agent is present in an amount of 0.1 to 3 parts by weight.

5. A tablet according to claim 1, wherein the lubricant is magnesium stearate.

6. A tablet according to claim 1, wherein the coating comprises a polymethacrylate as the hydrophobic pharmaceutical film former, triethyl citrate as a softener, and at least one pore-forming agent selected from the group consisting of polyethylene glycol 6000 and hydroxypropylmethyl cellulose (HPMC).

7. A tablet according to claim 6, wherein the coating further comprises talcum.

8. A tablet according to claim 6, wherein relative to the matrix core as 100 parts by weight, the coating contains 0.1 to 1 part by weight polymethacrylate, 0.05 to 0.5 parts by weight triethyl citrate, 0.01 to 0.5 parts by weight polyethylene glycol 6000, and 0.01 to 0.5 parts by weight hydroxypropylmethyl cellulose.

9. A tablet according to claim 1, wherein the matrix film tablet including the coating has a tablet strength with a total weight of active-substance content of the mixture of natural conjugated equine estrogens selected from the group consisting of 0.3 mg, 0.625 mg, 0.9 mg, 1.25 mg and 2.5 mg.

10. A tablet according to claim 9, wherein the tablet strength is 0.3 mg.

11. A tablet according to claim 9, wherein the tablet strength is 0.625 mg.

12. A tablet according to claim 1, wherein the matrix film tablet is provided with a sugar coating.

13. A method of producing a matrix film tablet with controlled active-substance release, said method comprising:
(a) preparing a preformulated dry extract of:
a natural mixture of conjugated equine estrogens which is present in the form of a pharmaceutically homogeneous dry extract; wherein said extract achieves a standardized amount of the natural mixture of conjugated equine estrogens per amount of support material defined relative to the main hormone constituents of the mixture, and
wherein said extract is produced by applying a natural conjugated equine estrogen mixture to a powdered or granular pharmaceutical support material selected from the group consisting of microcrystalline celluloses and mixtures of microcrystalline cellulose with lactose, by spraying an aqueous solution of the mixture onto the support material and thereafter drying;
(b) mixing together:
(i) the preformulated dry extract from step (a) above;
(ii) at least one gel-forming pharmaceutical polymeric matrix former;
wherein the gel-forming pharmaceutical polymeric matrix former is present in an amount of 20 to 50 parts by weight and selected from the group consisting of hydroxypropyl cellulose (HPC) hydroxypropylmethyl cellulose (HPMC) and carboxymethyl cellulose (CMC); and
(iii) optionally, one or more further pharmaceutical auxiliary substances selected from the group consisting of microcrystalline cellulose support materials, fillers, water-soluble osmotic agents, binders and lubricants;
wherein the other matrix former is microcrystalline cellulose present in an amount of 10 to 30 parts by weight; and
wherein the water-soluble agent is lactose present in an amount of 40 to 70 parts by weight; and
(c) compressing the mixture obtained in (b) in a tabletting machine to form matrix cores, and
(d) coating the matrix cores obtained in (c) with a film composition which comprises at least one hydrophobic pharmaceutical film former and optionally at least one auxiliary substance selected from the group consisting of pharmaceutical softeners and pore-forming agents;
wherein the matrix film tablet has one of the following release profile with an active-substance release measured as the total of estrone and equilin:
(i) 19% to 49% in 2 hours, 66% to 96% in 5 hours and greater than 80% after 8 hours; or
(ii) 12% to 37% in 2 hours, 57% to 85% in 5 hours and greater than 80% after 8 hours; or
(iii) 3% to 22% in 2 hours, 37% to 67% in 5 hours, 6% to 96% on 8 hours and greater than 80% after 12 hours.

14. The method according to claim 13, wherein the mixture obtained under (b) is granulated prior to compression in the tabletting machine.

15. The method according to claim 13, wherein mixture of (b) further comprises a polymer solution.

16. The method according to claim 15, wherein said polymer solution comprises a hydroxypropylmethyl cellulose solution or a hydroxypropylmethyl cellulose solution.

17. The method according to claim 13, further comprising applying a sugar coating to the matrix film tablets.

18. The method according to claim 13, wherein the main hormone constituents, relative to which the standardized amount of the natural mixture of conjugated equine estrogens per amount of support material is defined, comprise estrone, equilin and 17-α-dihydroequilin, and optionally 17-α-estradiol and 17-β-dihydroequilin, in their conjugated and free forms.

19. The method according to claim 13, wherein standardized amount of the natural mixture of conjugated equine estrogens per amount of support material is calculated either:
as the dry matter of an extract containing the mixture of conjugated equine estrogens from pregnant mares' urine including the free estrogens and other solids relative to the amount of the pharmaceutical support material in the pharmaceutically preformulated homogeneous dry extract, or
as the total hormone content comprising the conjugated and the free estrogens from pregnant mares' urine relative to the amount of the pharmaceutical support material in the pharmaceutically preformulated homogeneous dry extract.

20. The method of claim 13, wherein the aqueous solution comprises about 3.5% to about 20% by weight calculated as dry matter of the mixture of natural conjugated equine estrogens.

21. The method of claim 13, wherein the aqueous solution comprises 10 mg to about 100 mg total hormone content of the natural conjugated equine estrogen per gram of the aqueous solution.

22. The tablet of claim 1, wherein mixture of natural conjugated equine estrogens calculated as dry matter in the preformulated dry extract is about 0.25 to about 0.70 g per g the pharmaceutical support material.

23. The tablet of claim 1, wherein mixture of natural conjugated equine estrogens calculated as dry matter in the preformulated dry extract is about 0.28 to about 0.64 g per g the pharmaceutical support material.

24. The tablet of claim 1, wherein the total hormone content of the conjugated estrogen in the preformulated dry extract is about 35 mg to about 100 mg per g of the pharmaceutical support material.

25. The tablet of claim 1, wherein the total hormone content of the conjugated estrogen in the preformulated dry extract is about 43 mg to about 90 mg per g of the pharmaceutical support material.

* * * * *